United States Patent
Uchida et al.

(10) Patent No.: US 11,060,600 B2
(45) Date of Patent: Jul. 13, 2021

(54) EXTERNAL MECHANISM FOR ENDOSCOPE AND ENDOSCOPE APPARATUS

(71) Applicant: OLYMPUS CORPORATION, Tokyo (JP)

(72) Inventors: Ramiya Uchida, Tachikawa (JP); Masanobu Koitabashi, Hachioji (JP); Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/102,682

(22) Filed: Nov. 24, 2020

(65) Prior Publication Data
US 2021/0095753 A1    Apr. 1, 2021

Related U.S. Application Data

(63) Continuation of application No. PCT/JP2019/007368, filed on Feb. 26, 2019.

(30) Foreign Application Priority Data

May 29, 2018 (JP) .............................. JP2018-102347

(51) Int. Cl.
*F16H 57/02* (2012.01)
*A61B 1/00* (2006.01)
(Continued)

(52) U.S. Cl.
CPC ........... *F16H 57/031* (2013.01); *A61B 1/005* (2013.01); *A61B 1/0016* (2013.01);
(Continued)

(58) Field of Classification Search
CPC ......... F16H 57/031; F16H 2057/02039; A61B 1/00112; A61B 1/00133; A61B 1/0016; A61B 1/005; A61B 1/0052; A61B 1/0057
See application file for complete search history.

(56) References Cited

U.S. PATENT DOCUMENTS

2020/0367725 A1* 11/2020 Okamoto ........... A61B 1/00016
2020/0397226 A1* 12/2020 Okamoto ............... G02B 23/24
(Continued)

FOREIGN PATENT DOCUMENTS

| JP | 2-55907 U | 4/1990 |
|---|---|---|
| JP | 3222190 B2 | 10/2001 |

(Continued)

OTHER PUBLICATIONS

International Search Report dated May 21, 2019 received in PCT/JP2019/007368.

*Primary Examiner* — Adam D Rogers
(74) *Attorney, Agent, or Firm* — Scully, Scott, Murphy & Presser, P.C.

(57) ABSTRACT

An external mechanism for endoscope includes: an abutment surface that is a first surface configured to cover a knob arranging surface at which a second bending operation knob is arranged in an operation portion of an endoscope; a wheel configured to engage with the second bending operation knob arranged at the knob arranging surface; a motor configured to generate a driving force for rotating the wheel; a housing case that houses the wheel and the motor; a case attaching/detaching and fixing section for detachably attaching the housing case to the operation portion of the endoscope; and a locking member provided at the housing case and configured to be locked on the knob arranging surface of the endoscope and a large-diameter portion end face adjacent to the knob arranging surface in the operation portion of the endoscope.

6 Claims, 12 Drawing Sheets

(51) Int. Cl.
  *F16H 57/031*   (2012.01)
  *A61B 1/005*    (2006.01)
(52) U.S. Cl.
  CPC ...... *A61B 1/00112* (2013.01); *A61B 1/00133* (2013.01); *F16H 2057/02039* (2013.01)

(56) References Cited

U.S. PATENT DOCUMENTS

| | | | |
|---|---|---|---|
| 2020/0397227 A1* | 12/2020 | Okamoto | A61B 1/0052 |
| 2021/0063723 A1* | 3/2021 | Uchida | G02B 23/2461 |
| 2021/0105385 A1* | 4/2021 | Uchida | H04N 5/2253 |

FOREIGN PATENT DOCUMENTS

| | | | | |
|---|---|---|---|---|
| JP | 2008-048788 A | 3/2008 | | |
| JP | 3181928 U | 2/2013 | | |
| WO | WO-2019234990 A1 * | 12/2019 | | A61B 1/005 |
| WO | WO-2020144731 A1 * | 7/2020 | | A61B 1/00 |

* cited by examiner

EXTERNAL MECHANISM FOR ENDOSCOPE AND ENDOSCOPE APPARATUS

CROSS REFERENCE TO RELATED APPLICATION

This application is a continuation application of PCT/JP2019/007368 filed on Feb. 26, 2019 and claims benefit of Japanese Application No. 2018-102347 filed in Japan on May 29, 2018, the entire contents of which are incorporated herein by this reference.

BACKGROUND OF THE INVENTION

1. Field of the Invention

The present invention relates to an external mechanism for endoscope, the external mechanism being detachably attachable to a bending operation knob of an endoscope and bending a bending portion provided in an insertion portion by turning the knob with a driving force of a motor unit, and an endoscope apparatus including the external mechanism for endoscope.

2. Description of the Related Art

Endoscopes have been used in, e.g., a medical field and an industrial field. Each endoscope includes a bending portion in an elongated insertion portion configured to be inserted into a subject/object.

Japanese Patent Application Laid-Open Publication No 2008-48788 discloses an endoscope including a first bending portion and a second bending portion aligned in a direction of extension of an elongated insertion portion on a distal end side of the insertion portion, in which a main bending operation device and a sub-bending operation device are provided at an operation portion located on a proximal end side of the insertion portion. In such endoscope, an operation of bending the first bending portion is performed by turning an operation knob of the main bending operation device, and an operation of bending the second bending portion is performed by turning an operation knob of the sub-bending operation device.

Therefore, a user can insert the insertion portion smoothly into an intricately flexed lumen and can also easily head an observation optical system incorporated on the distal end side of the insertion portion in a desired direction, by turning the respective operation knobs individually to bend the first bending portion or the second bending portion.

In the operation portion disclosed in Japanese Patent Application Laid-Open Publication No. 2008-48788, the sub-bending operation device is provided on the proximal end side of the operation portion, which is the side opposite to the insertion portion, relative to the main bending operation device, and is spaced from the main bending operation device. Therefore, it is difficult for the user to smoothly switch between an operation of turning the main bending operation device and an operation of turning a sub-bending operation device with fingers of a hand grasping the operation portion. Moreover, when the user performs an operation of turning a knob of a bending operation device, a large burden is placed on the fingers of the hand of the user.

In view of the point, an external electric bending mechanism that is attachable/detachable to/from an operation portion, and in an attached state, for example, turns a sub-bending operation device via a driving force of a drive source such as a motor has been devised.

For example, Japanese Patent No. 3222190 discloses a bending control device that by being fitted to an endoscope body, enables using a manual bending-type endoscope as an electric angle control-type endoscope. The bending control device for endoscope is fitted by integrating a body portion of the bending control device attached to the angle knob side of an operation portion and an attachment plate provided so as to face the body portion across the operation portion, via fastening screws so as to cover an entire periphery of the operation portion.

SUMMARY OF THE INVENTION

An external mechanism for endoscope according to an aspect of the present invention includes: a first surface configured to cover a knob arranging surface at which a bending operation knob is arranged in an operation portion of an endoscope; an engaging member configured to engage with the bending operation knob of the endoscope, the bending operation knob being arranged on the knob arranging surface; a drive source configured to generate a driving force for rotating the engaging member; a housing case that houses the engaging member and the drive source; a case attaching/detaching and fixing section for detachably attaching the housing case to the operation portion of the endoscope; and a locking member provided at the housing case and configured to be locked on the knob arranging surface of the endoscope and a surface adjacent to the knob arranging surface in the operation portion of the endoscope.

An endoscope apparatus according to an aspect of the present invention includes: an endoscope that includes an operation portion including a bending operation knob configured to perform an operation of bending a bending portion, and a knob arranging surface at which the bending operation knob is arranged; and an external mechanism for endoscope, the external mechanism including a first surface configured to cover the knob arranging surface of the endoscope, an engaging member configured to engage with the bending operation knob of the endoscope, the bending operation knob being arranged at the knob arranging surface, a drive source configured to generate a driving force for rotating the engaging member, a housing case that houses the engaging member and the drive source, a case attaching/detaching and fixing section for detachably attaching the housing case to the operation portion of the endoscope, and a locking member provided at the housing case and configured to be locked on the knob arranging surface of the endoscope and a surface adjacent to the knob arranging surface in the operation portion of the endoscope.

DETAILED DESCRIPTION OF THE PREFERRED EMBODIMENT

Figure 1:
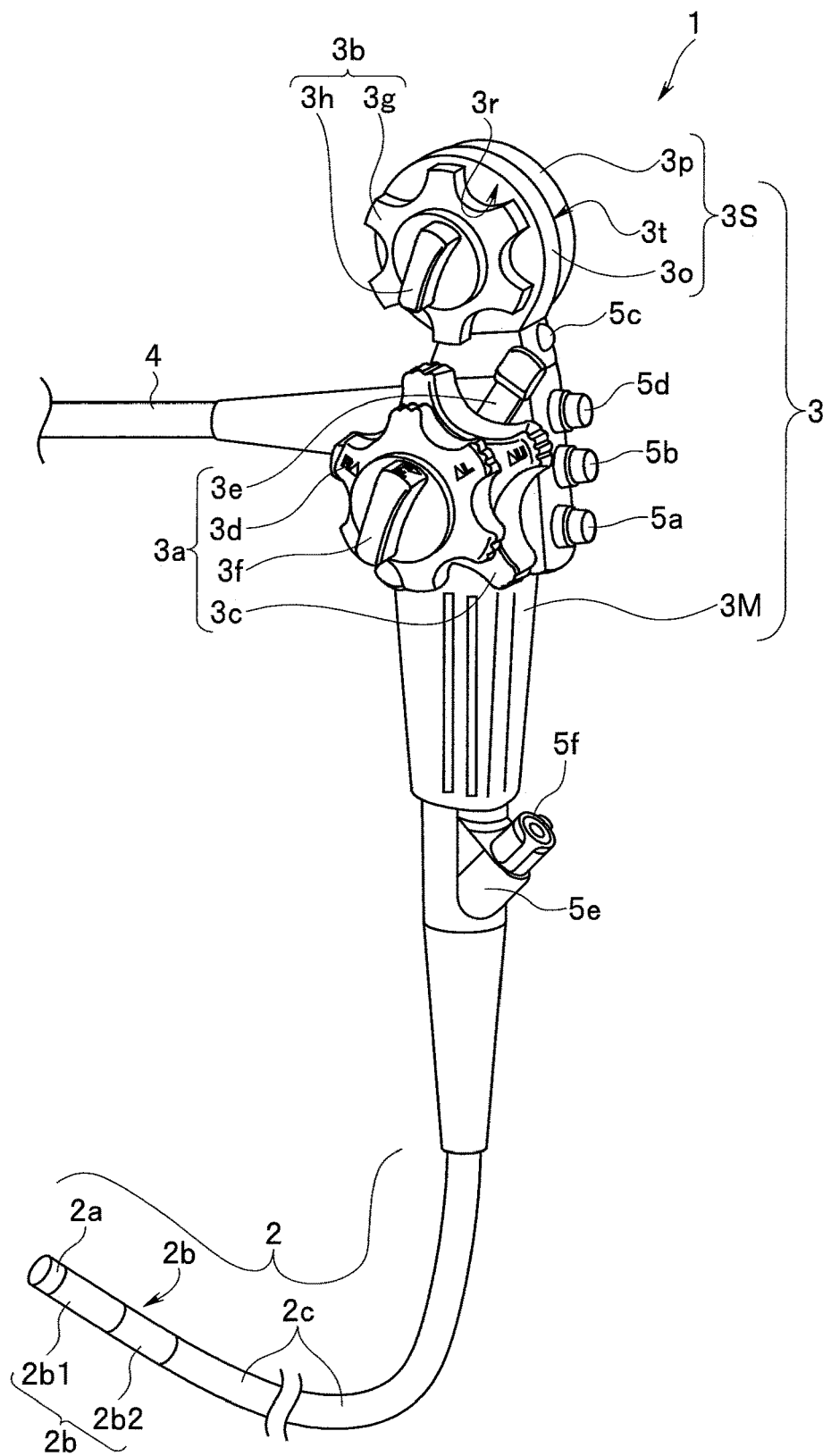
FIG. 1 is a diagram illustrating an example configuration of an endoscope.

An embodiment of the present invention will be described below with reference to the drawings.

Note that in each of the drawings used for the below description, in order to illustrate respective components in sizes that are large enough to be recognized in the drawings, some of the components are illustrated so as to be different in scale. In other words, the present invention is not limited only to the counts and amounts of the components, shapes of the components, ratios in size between the components and relative positional relationships between the respective components indicated in the drawings.

A configuration of an endoscope will be described with reference to FIG. 1.

An endo scope 1, which is illustrated in FIG. 1, includes an elongated insertion portion 2, an operation portion 3 that doubles as a grasping portion, and a universal cord 4. In the insertion portion 2, a distal end portion 2a, a bending portion 2b and a flexible tube portion 2c that is long and flexible are provided continuously in the order mentioned from the distal end side.

In the present embodiment, the bending portion 2b includes a first bending portion 2b1 and a second bending portion 2b2. The first bending portion 2b1 is provided on the distal end side of the insertion portion 2. The second bending portion 2b2 is provided so as to be continuous with a proximal end portion of the first bending portion 2b1 via a link portion (not illustrated). The first bending portion 2b1 is bendable, for example, in upward, downward, rightward and leftward directions. On the other hand, the second bending portion 2b2 are bendable in the upward and downward directions.

The operation portion 3 includes a first bending operation device 3a and a second bending operation device 3b. In the present embodiment, the operation portion 3 includes a main operation portion 3M that doubles as a grasping portion and is provided with the first bending operation device 3a, and a sub-operation portion 3S that is provided on the proximal end side of the main operation portion 3M and includes a second bending operation device 3b. The second bending operation device 3b is provided away from the first bending operation device 3a, on the proximal end side of the operation portion, which is the side opposite to the insertion portion 2.

The first bending operation device 3a includes a first bending portion upward/downward operation knob (hereinafter abbreviated as "first UD knob") 3c and a first bending portion rightward/leftward operation knob (hereinafter abbreviated as "first RL knob") 3d as bending operation knobs, a first bending portion upward/downward direction fixing lever (hereinafter abbreviated as "first UD fixing lever") 3e and a first bending portion rightward/leftward direction fixing handle (hereinafter abbreviated as "first RL fixing handle") 3f.

The second bending operation device 3b includes a second bending portion upward/downward operation knob (hereinafter abbreviated as "second UD knob") 3g, which is a bending operation knob, and a second bending portion upward/downward direction fixing handle (hereinafter abbreviated as "second UD fixing handle") 3h.

The sub-operation portion 3S includes a large-diameter portion 3o having a predetermined outer diameter, and a small-diameter portion 3p having an outer diameter that is smaller than the outer diameter of the large-diameter portion 3o. Reference numeral 3r denotes a knob arranging surface. On the knob arranging surface 3r, the second UD knob 3g is disposed.

The large-diameter portion 3o and the small-diameter portion 3p are concentric to each other, and reference numeral 3t denotes a large-diameter portion end face. The large-diameter portion end face 3t is a second surface adjacent to the knob arranging surface 3r across the large-diameter portion 3o and is a surface opposite to the knob arranging surface 3r. The small-diameter portion 3p protrudes from the large-diameter portion end face 3t. Therefore, the large-diameter portion end face 3t is arranged so as to surround a circumference of the small-diameter portion 3p and has a function as a later-described locking surface.

The first UD knob 3c is turned for bending the first bending portion 2b1 in the upward/downward directions. The first RL knob 3d is turned for bending the first bending portion 2b1 in the rightward/leftward directions. The first UD fixing lever 3e is switchable between a free position and a fixing position. The first RL fixing handle 3f is switchable between a free position and a fixing position.

When the first UD fixing lever 3e is in the free position, the first UD knob 3c is turnable. At this time, the first bending portion 2b1 bends in the upward direction or the downward direction along with an operation of turning the first UD knob 3c. On the other hand, when the first RL fixing handle 3*f* is in the free position, the first RL knob 3*d* is turnable. At this time, the first bending portion 2*b*1 bends in the rightward direction or the leftward direction along with an operation of turning the first RL knob 3*d*.

On the other hand, when the first UD fixing lever 3*e* is switched to the fixing position, turning of the first UD knob 3*c* is restricted. As a result, a bending state in the upward/downward direction of the first bending portion 2*b*1 is kept in the state at the time of the switching. Likewise, when the first RL fixing handle 3*f* is switched to the fixing position, turning of the first RL knob 3*d* is restricted. As a result, a bending state in the rightward/leftward direction of the first bending portion 2*b*1 is kept in the state at the time of the switching.

The second UD knob 3*g* is turned for bending the second bending portion 2*b*2 in the upward/downward directions. The second UD fixing handle 3*h* is switchable between a free position and a fixing position.

When the second UD fixing handle 3*h* is in the free position, the second UD knob 3*g* is turnable. At this time, the second bending portion 2*b*2 bends in the upward direction or the downward direction along with an operation of turning the second UD knob 3*g*. On the other hand, when the second UD fixing handle 3*h* is switched to the fixing position, turning of the second UD knob 3*g* is restricted. As a result, a bending state in the upward/downward direction of the second bending portion 2*b*2 is kept in the state at the time of the switching.

Note that reference numeral 5*a* denotes an air/water feeding button, reference numeral 5*b* denotes a suction operation button, reference numerals 5*c*, 5*d* each denote a remote switch, reference numeral 5*e* denotes a treatment instrument insertion opening and reference numeral 5*f* denotes a forceps plug. The remote switches are switches for, e.g., stopping or recording of an endoscopic image displayed on a screen of a display device (not illustrated), enlargement of the image or switching of illuminating light, and an optimum function is assigned to each of the switches.

Figure 2A:
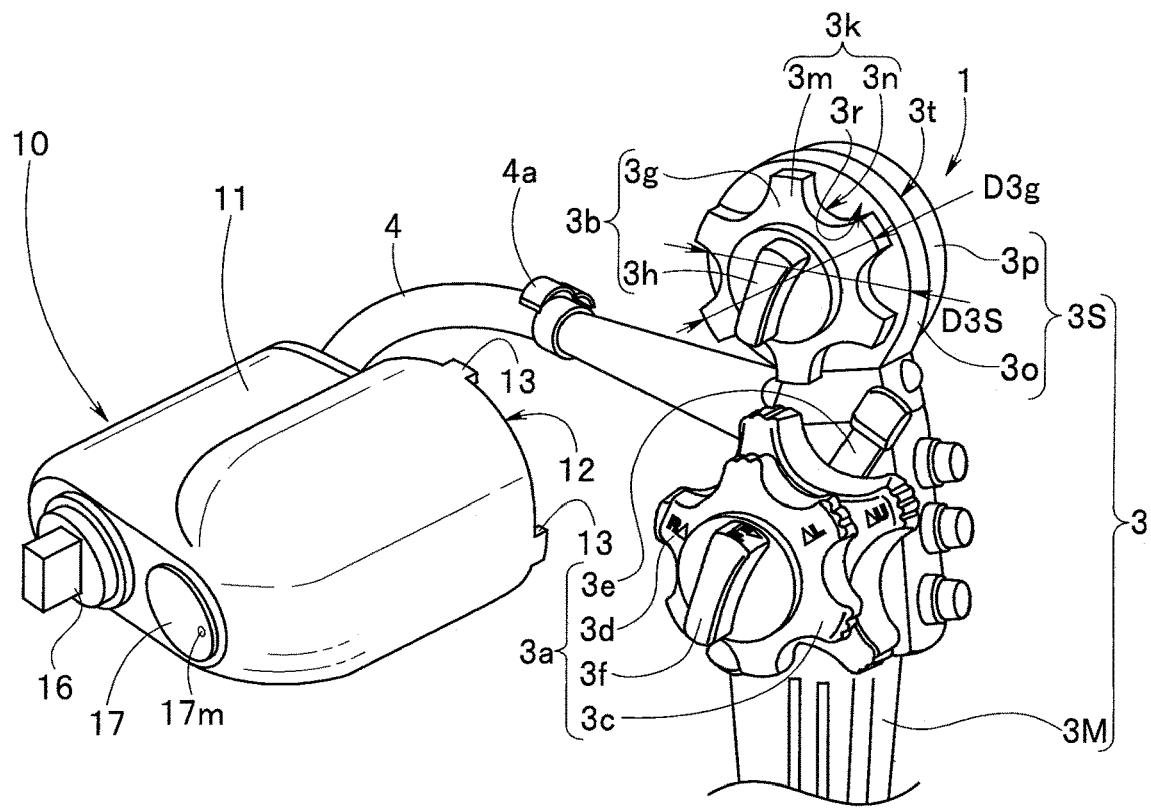
FIG. 2A is a diagram illustrating a relationship between a sub-operation portion included in an operation portion of the endoscope and an external mechanism for endoscope.

Reference numeral 10 in FIG. 2A denotes an external mechanism for endoscope. The external mechanism for endoscope 10 configures a part of an endoscope apparatus by being attached to the endoscope 1. The external mechanism for endoscope 10 includes a housing case 11, and inside the housing case 11, a bending wheel (see reference numeral 41 in FIG. 5B mentioned later), which is detachably attachable to the second UD knob 3*g* provided in the sub-operation portion 3S, is disposed. The external mechanism for endoscope 10 is an auxiliary mechanism unit configured to turn the bending wheel attached to the second UD knob 3*g* by means of a driving force of a later-described motor (see reference numeral 32 in FIG. 5B mentioned later) to make the second UD knob 3*g* operate.

Reference numeral 12 denotes a case attaching/detaching and fixing section (hereinafter referred to as "case attaching/detaching section").

The housing case 11 is made of a resin and a plurality of locking members 13 are provided at the case attaching/detaching section 12. The locking members 13 can provide a locked state by being arranged on the large-diameter portion end face 3*t* of the sub-operation portion 3S, the large-diameter portion end face 3*t* having a function as a locking surface. Reference numeral 16 denotes a switching handle, and reference numeral 17 denotes a bending state display section including a rotation indicator 17*m*.

Figure 2B:
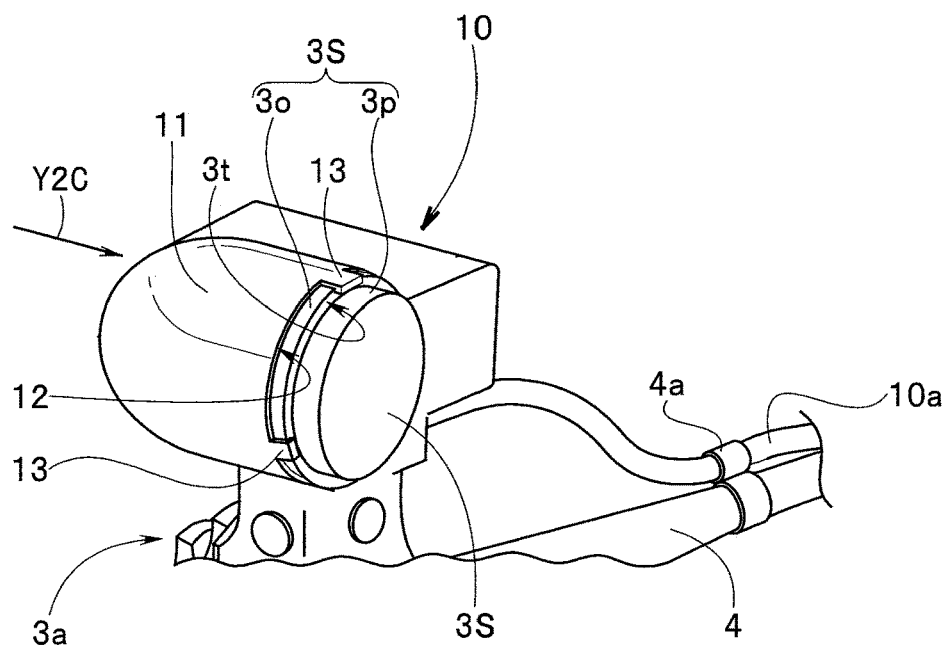
FIG. 2B is a diagram illustrating a state in which the external mechanism for endoscope is arranged on the sub-operation portion.

Reference numeral 4*a* denotes a cable attaching bracket, and as illustrated in FIG. 2B, each of one or more cable attaching brackets is provided at a desired position on the universal cord 4 for attachment of an electric cable 10*e*.

Figure 2C:
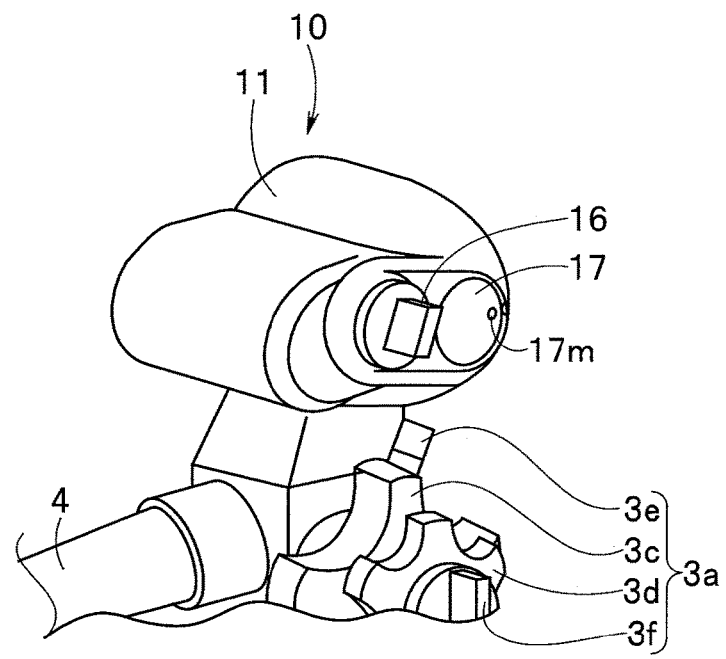
FIG. 2C is a view of the sub-operation portion in FIG. 2B from the arrow Y2C side.

As illustrated in FIGS. 2B and 2C, the housing case 11 of the external mechanism for endoscope 10 covers the second UD knob 3*g*. In the covering state, as illustrated in FIG. 2B, the locking members 13 of the case attaching/detaching section 12 of the case 11 are attached to the sub-operation portion 3S in an integrated manner by being locked on the large-diameter portion end face 3*t* of the sub-operation portion 3S.

A configuration of the external mechanism for endoscope 10 will be described.

Figure 3:
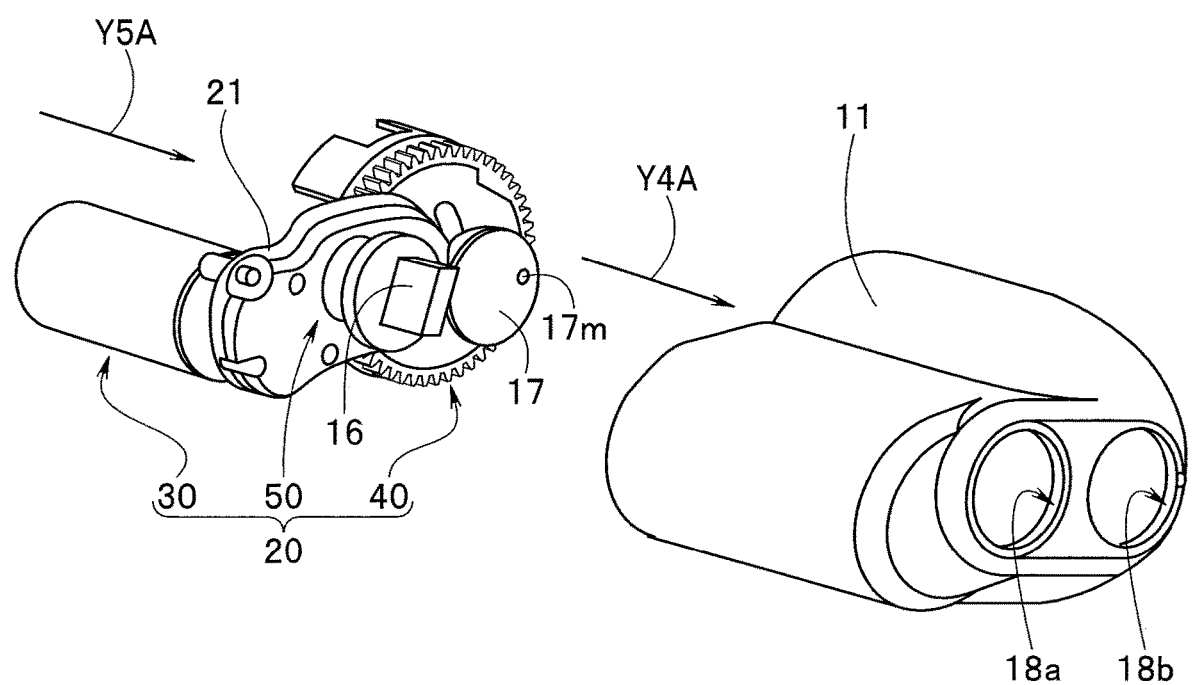
FIG. 3 is a diagram illustrating a relationship between a housing case of the external mechanism for endoscope and a knob rotation mechanism housed in the housing case.
Figure 4A:
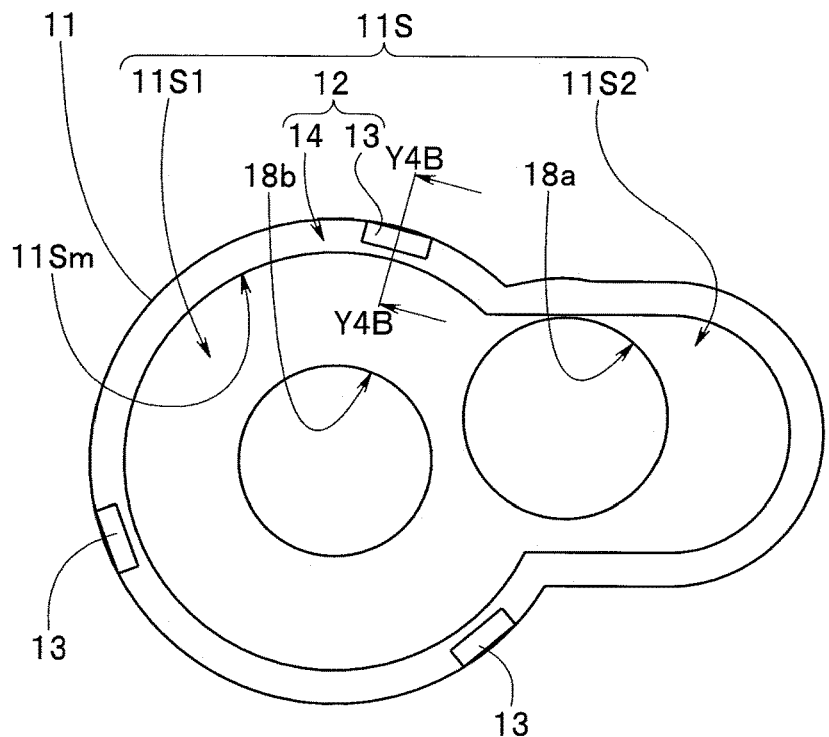
FIG. 4A is a front view of the housing case as the housing case in FIG. 3 is viewed in the arrow Y4A direction.

The housing case 11 of the external mechanism for endoscope 10 illustrated in FIG. 3 includes a case inner space 11S, which is illustrated in FIG. 4A. A knob rotation mechanism 20, which is illustrated in FIG. 3, is housed in the case inner space 11S.

As illustrated in FIG. 4A, the case inner space 11S mainly includes an engaging member disposing space 11S1 and a drive source disposing space 11S2. An opening 11S*m* of the engaging member disposing space 11S1 is a part of an opening provided in the above-described case attaching/detaching section 12 and is also an opening of a knob rotating unit housing hole portion 11*h*.

As illustrated in FIGS. 3 and 4A, in the housing case 11, a first through-hole 18*a* in which the switching handle 16 is disposed and a second through-hole 18*b* in which the bending state display section 17 is disposed are provided. The first through-hole 18*a* brings the drive source disposing space 11S2 and the outside into communication with each other and the second through-hole 18*b* brings the engaging member disposing space 11S1 and the outside into communication with each other.

As illustrated in FIG. 4A, the case attaching/detaching section 12 includes the plurality of locking members 13 and an abutment surface 14, which is a first surface. The plurality of locking members 13 are provided at respective predetermined positions in the abutment surface 14 having an annular shape at predetermined intervals or regular intervals in a circumferential direction. Note that the number of locking members 13 is not limited to three and may be more than three, or two.

Figure 4B:
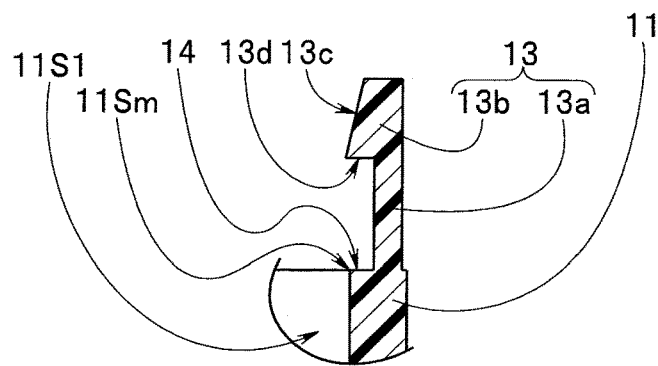
FIG. 4B is a sectional view along the arrow Y4B-Y4B line in FIG. 4A and is a diagram illustrating a locking member.

As illustrated in FIG. 4B, each locking member 13 is what is called a locking claw and protrudes by a predetermined dimension from the abutment surface 14 along a center axis (not illustrated) of the engaging member disposing space 11S1. The abutment surface 14 is arranged in abutment with the knob arranging surface 3*r* and covers the knob arranging surface 3*r*.

Each locking member 13 includes an elastically deforming portion 13*a* and an engaging portion 13*b* on the order mentioned from the abutment surface 14 side. Each locking member 13 is formed such that the elastically deforming portion 13*a* elastically deforms into a predetermined manner.

Reference numeral 13*c* denotes a guiding surface that is an inclined surface. The engaging portion 13*b* has a tapered shape in which the distal end side is reduced in size. Reference numeral 13*d* is an engagement surface.

Figure 4C:
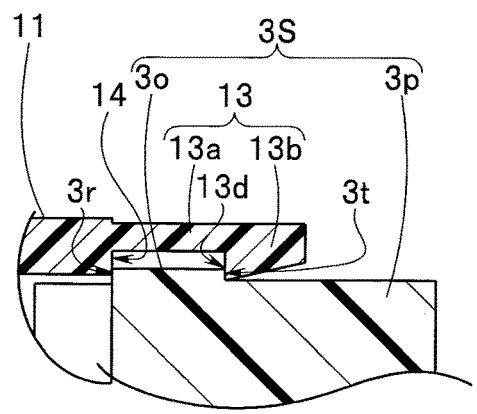
FIG. 4C is a diagram illustrating operation of a locking member and is a diagram illustrating a relationship between a locking member and a sub-operation portion.

The abutment surface 14 abuts on the knob arranging surface 3*r* of the sub-operation portion 3S illustrated in FIG. 2A. On the other hand, the engagement surface 13*d* abuts on the large-diameter portion end face 3*t*. As illustrated in FIG. 4C, in an engaged state in which the abutment surface 14 is in abutment with the knob arranging surface 3*r* and the engagement surface 13*d* is in abutment with the large-diameter portion end face 3*t*, the housing case 11 is fixedly provided on the sub-operation portion 3S.

Here, the knob rotation mechanism 20 will be described with reference to FIGS. 3, 5A and 5B.

As illustrated in FIG. 3, the knob rotation mechanism 20 mainly includes a motor section 30, a knob rotating unit 40 and a transmission section 50. Reference numeral 21 in FIGS. 3, 5A and 5B is a rotation mechanism unit body and is also an attachment member.

Figure 5A:
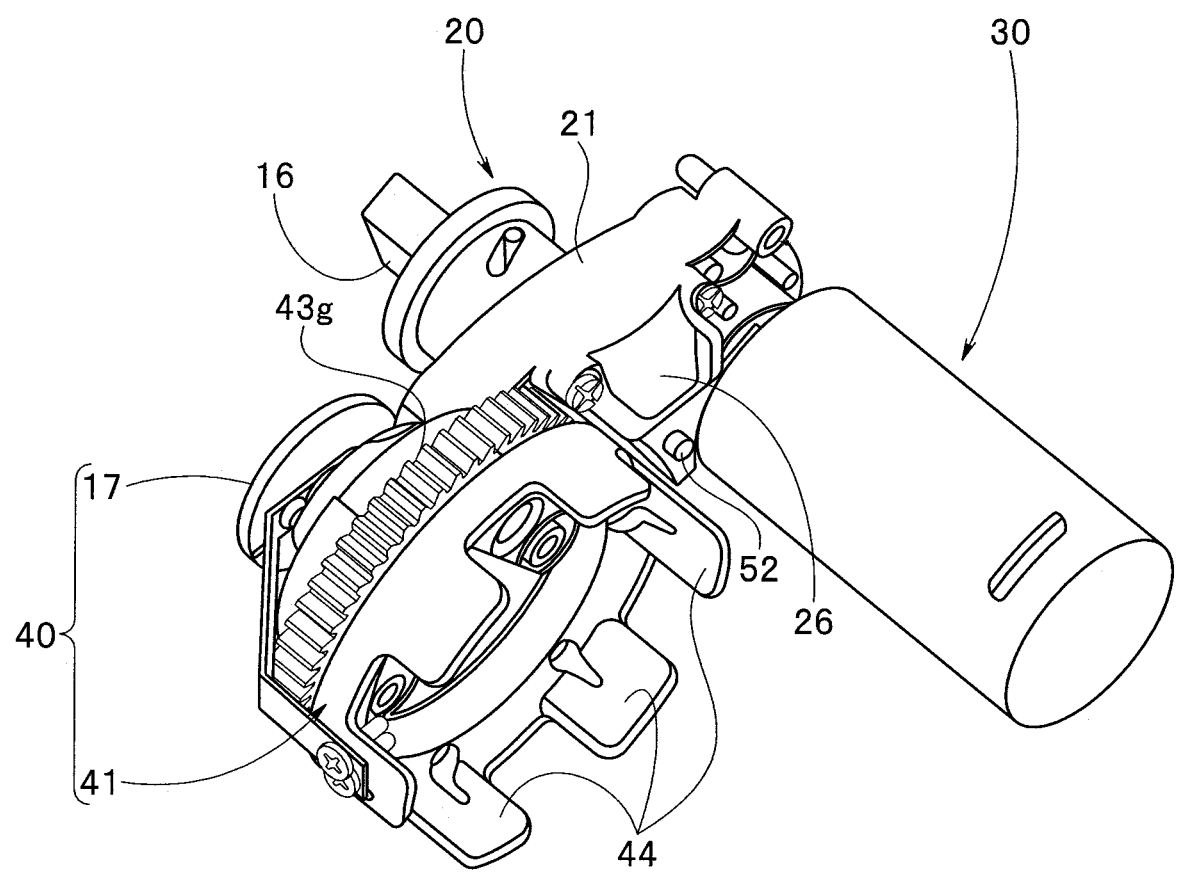
FIG. 5A is a view of the knob rotation mechanism in the arrow Y5A direction in FIG. 3.
Figure 5B:
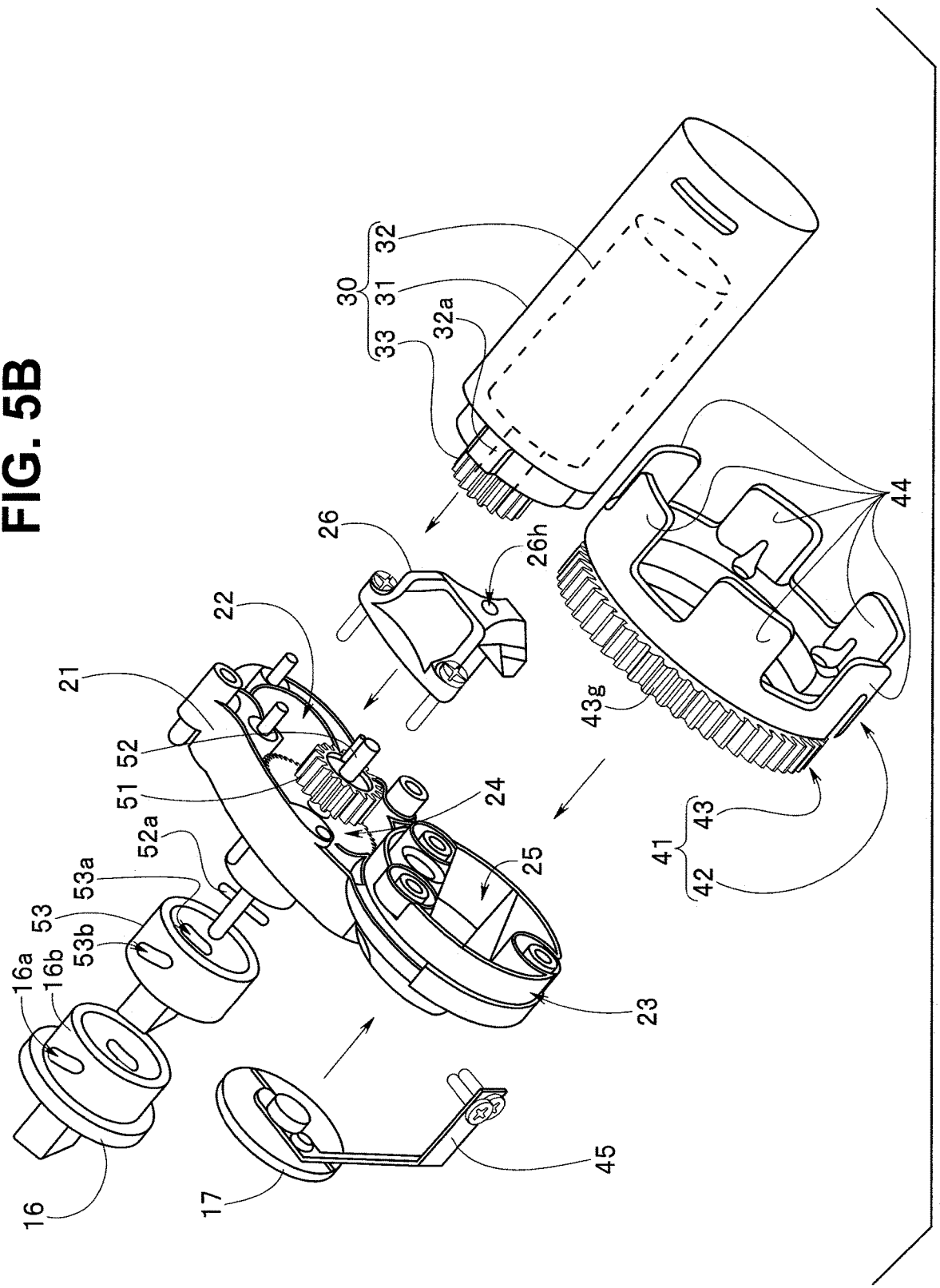
FIG. 5B is an exploded perspective diagram illustrating an overview of a configuration of the knob rotation mechanism.

As illustrated in FIG. 5B, in the rotation mechanism unit body 21, e.g., a motor attaching portion 22, a wheel attaching portion 23 and a switching gear attaching portion 24 are provided at respective predetermined positions.

Reference numeral 25 denotes a recess portion for handle, which is a hole formed so as to have an outer shape and a depth that enable receiving the second UD fixing handle 3*h*. Reference numeral 26 denotes a switching gear supporting member including a through-hole 26*h* in which one end portion of a switching gear shaft 52 with a switching gear 51 fixedly provided is disposed.

The switching gear supporting member 26 is fixedly provided at a predetermined position in the rotation mechanism unit body 21 and turnably supports the one end portion of the switching gear shaft 52 disposed in the through-hole 26*h*.

The motor section 30 mainly includes a motor case 31, a motor 32, which is a drive source indicated by dashed lines, and a drive gear 33. The motor 32 is disposed inside the motor case 31. The drive gear 33 is fixedly provided on a motor shaft 32*a* that protrudes from the motor 32.

As illustrated in FIG. 5A, the motor case 31 is fixedly provided in a predetermined manner in the motor attaching portion 22 illustrated in FIG. 5B.

As illustrated in FIGS. 5A and 5B, the knob rotating unit 40 includes a bending wheel 41 and a bending state display section 17. The bending wheel 41 is a ring-like member and is also an engaging member configured to engage with the second UD knob 3*g*. The bending wheel 41 includes a knob joining portion 42 and a mesh section 43, and the knob joining portion 42 and the mesh section 43 are fixed integrally.

The mesh section 43 is a gear section including a gear 43*g* on an outer peripheral surface. In the knob joining portion 42, a plurality of projection portions 44 are aligned in a circumferential direction. The plurality of projection portions 44 are configured to be received in respective recess portions 3*n* located among a plurality of projection portions 3*m* forming a projection and recess portion (reference numeral 3*k* in FIG. 2A) included in the second UD knob 3*g*.

By the projection portions 44 being disposed in the respective recess portions 3*n*, the second UD knob 3*g* and the bending wheel 41 are integrated. In the integrated state, along with rotation of the bending wheel 41, the second UD knob 3*g* is rotated in a direction of the rotation.

In the bending state display section 17, which is a circular plate, a rotation indicator 17*m* is provided at a predetermined position on a surface of the circular plate. Reference numeral 45 denotes a joining member. One end portion of the joining member 45 is fixedly provided so as to be integrated with a back surface of the bending state display section 17. The other end portion of the joining member 45 is fixedly provided at a predetermined position on an outer peripheral surface of the knob joining portion 42 included in the bending wheel 41, in an integrated manner.

Therefore, along with clockwise or counterclockwise rotation of the bending wheel 41, the bending state display section 17 is rotated in a direction that is the same as the direction of the rotation of the bending wheel 41. Therefore, a user can easily determine a bending angle (bending amount) of the second bending portion 2*b*2 by confirming a position of the rotation indicator 17*m*.

Figure 5C:
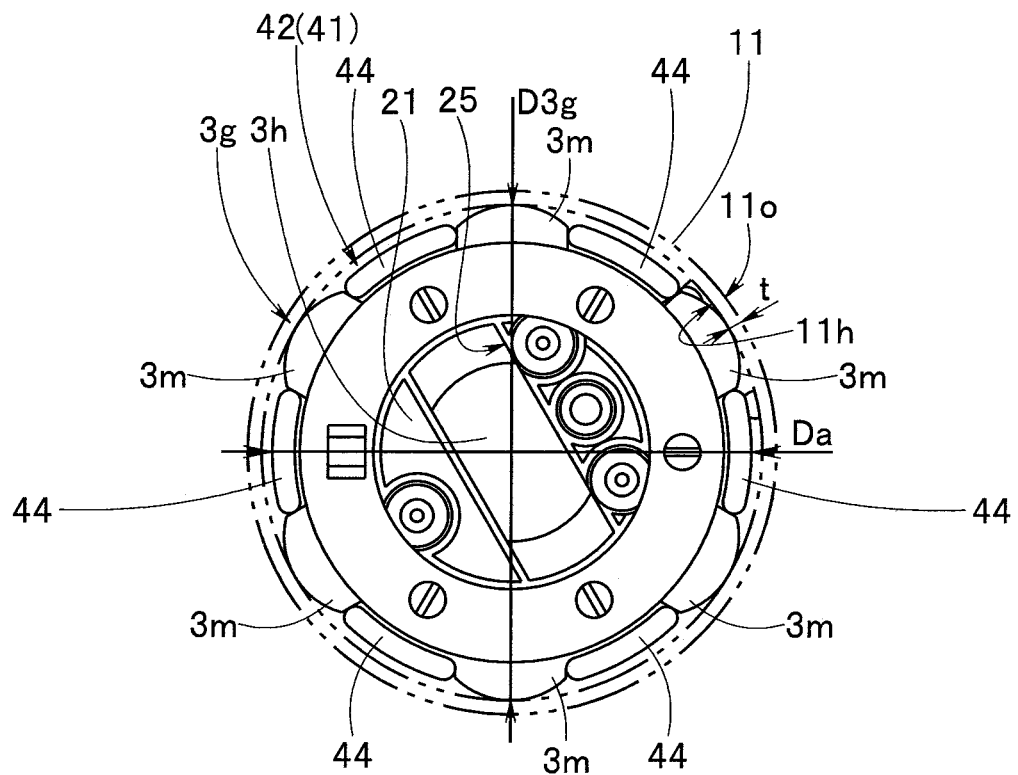
FIG. 5C is a diagram illustrating an attachment state in which projection portions of a knob joining portion are disposed in a predetermined manner inside respective recess portions of a second bending portion upward/downward operation knob.

In the present embodiment, as illustrated in FIG. 5C, an outer diameter Da of the knob joining portion 42 of the bending wheel 41 is set to be smaller than an outer diameter D3*g* of the second UD knob 3*g*. Then, as illustrated in FIG. 2A, in order for the second UD knob 3*g* to be arranged on the inner side relative to an outer peripheral surface (indicated as an outer periphery outer diameter D3S) of the sub-operation portion 3S, the outer diameter D3*g* of the second UD knob 3*g* is set to be smaller than the outer periphery outer diameter D3S in advance.

Therefore, in a state in which the bending wheel 41 is integrated with the second UD knob 3*g*, an outer peripheral surface of the bending wheel 41 is located on the center side relative to an outer peripheral surface of the second UD knob 3*g*.

Reference numeral 11*h* denotes an inner peripheral surface of the knob rotating unit housing hole portion of the housing case 11. An inner diameter of the inner peripheral surface 11*h* is set to be larger than the outer diameter D3*g* of the second UD knob 3*g* in advance. In addition, a thickness t of the housing case 11 is set such that an outer peripheral surface 11*o* of the knob rotating unit housing hole portion 11*h* and the outer peripheral surface of the sub-operation portion 3S are in flush with each other in a disposed state.

Note that the outer peripheral surface 11*o* of the knob rotating unit housing hole portion 11*h* may be set to be slightly larger than the outer peripheral surface of the sub-operation portion 3S.

In this way, the outer peripheral surface of the bending wheel 41 is set to be arranged on the center side relative to the outer peripheral surface of the second UD knob 3*g*. A thickness of the knob rotating unit housing hole portion 11*h* of the housing case 11 is appropriately set to set a diameter of the outer peripheral surface 11*o* of the knob rotating unit housing hole portion 11*h* to be equal to or slightly larger than a diameter of the outer peripheral surface of the sub-operation portion 3S.

As a result, in a state in which the housing case 11 with an outer shape of the housing case 11 reduced in size is disposed on the sub-operation portion 3S by the housing case 11 being put on the second UD knob 3*g*, it is possible to curb e.g., an operation of the first UD knob 3*c*, an operation of the first RL knob 3*d* and an operation of the first UD fixing lever 3*e* being adversely affected by the outer peripheral surface 11*o* of the knob rotating unit housing hole portion 11*h* of the housing case 11 largely protruding from the outer peripheral surface of the sub-operation portion 3S.

Figure 5D:
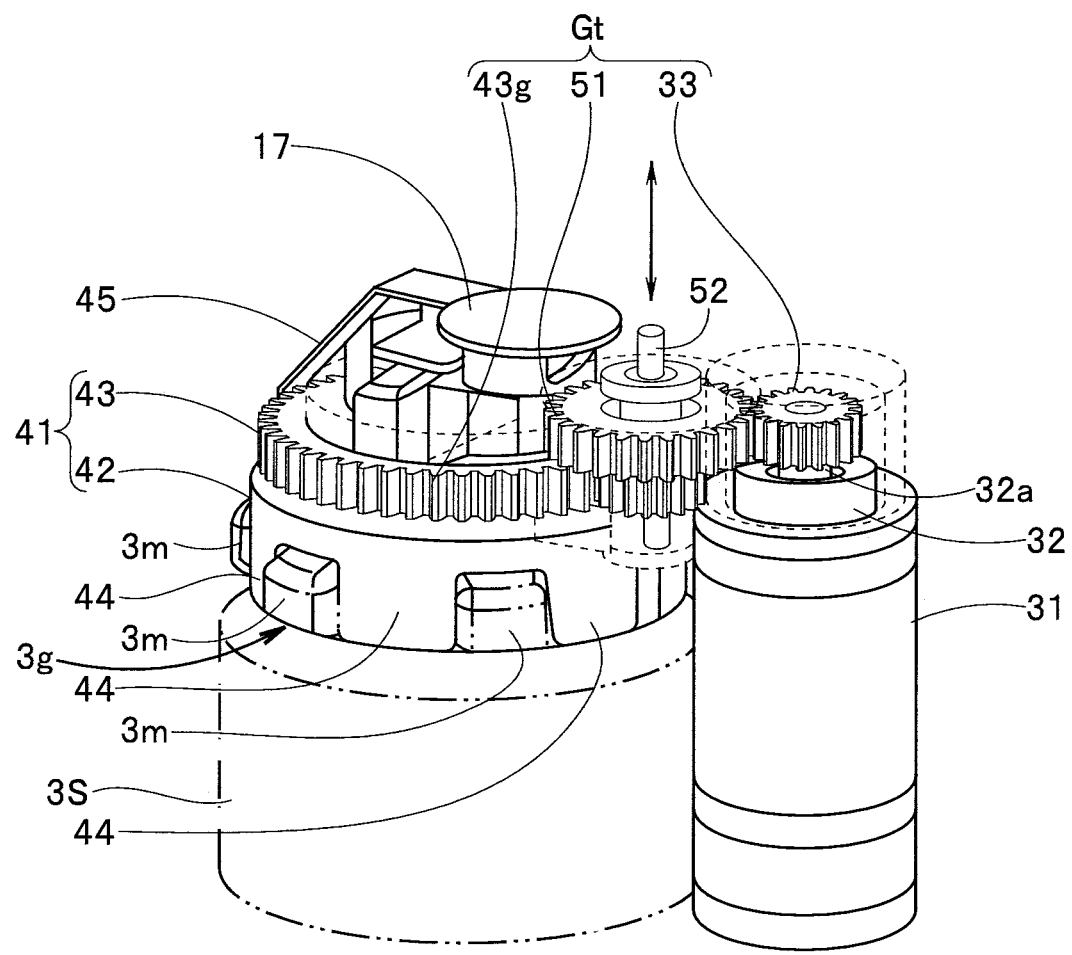
FIG. 5D is a diagram illustrating a gear train including a switching gear, a gear of a mesh section and a drive gear fixedly provided on a motor shaft.

The transmission section 50 mainly includes a switching gear 51, a switching gear shaft 52, a cam ring 53 and a switching handle 16, which are illustrated in FIG. 5B. As described above, the switching gear 51 is fixedly provided on the one end portion side of the switching gear shaft 52. The switching gear 51 forms a gear train Gt, which is illustrated in FIG. 5D, jointly with the gear 43*g* of the mesh section 43 of the above-described bending wheel 41 and the drive gear 33 fixedly provided on the motor shaft 32*a*.

As illustrated in FIG. 5B, at the other end portion of the switching gear shaft 52, an engaging lug 52*a* that protrudes in a direction orthogonal to the shaft 52 is provided. In the cam ring 53, a cam groove for ring 53*a* is formed. A lug for ring 53*b* protrudes from an outer peripheral surface of the cam ring 53. The switching handle 16 includes a cylindrical portion 16a, and in the cylindrical portion 16a, a cam groove for cylinder 16b is formed.

On the inner peripheral surface side of the cylindrical portion 16a of the switching handle 16, the outer peripheral surface side of the cam ring 53 is disposed. In this disposition state, the lug for ring 53b is arranged inside the cam groove for cylinder 16b. On the other hand, on the inner peripheral surface side of the cam ring 53, the engaging lug 52a is disposed. In this disposition state, the engaging lug 52a is arranged inside the cam groove for ring 53a.

With this configuration, along with rotation of the switching handle 16, the lug for ring 53b inside the cam groove for cylinder 16b is moved and the cam ring 53 is moved in an axis direction of the switching gear shaft 52. In addition, along with the movement in the axis direction of the cam ring 53, the engaging lug 52a inside the cam groove for ring 53a is moved in the axis direction.

As a result of the above, as illustrated in FIG. 5D, along with an operation of switching to clockwise or counterclockwise rotation of the switching handle 16, the switching gear 51 of the gear train Gt is moved in the axis direction of the switching gear shaft 52 to make switching to a state in which the switching gear 51, and the gear 43c of the mesh section 43 and the drive gear 33 mesh with each other or a state in which the switching gear 51, and the gear 43c of the mesh section 43 and the drive gear 33 are separated from each other.

Then, in a transmission state in which the switching gear 51, and the gear 43c of the mesh section 43 and the drive gear 33 mesh with each other, the second UD knob 3g is rotated by a rotation driving force of the motor 32 being transmitted to the bending wheel 41. In other words, the driving force of the motor 32 can be prevented from being transmitted to the bending wheel 41 by separating the switching gear 51, and the gear 43c of the mesh section 43 and the drive gear 33.

Note that although the illustration is omitted, the motor 32 is driven when the motor 32 receives a driving control signal outputted by operating an operation switch provided at the housing case 11 or a remote switch provided at the operation portion 3, and rotates the second UD knob 3g in a clockwise direction or a counterclockwise direction.

Attachment of the external mechanism for endoscope 10 to the sub-operation portion 3S will be described.

First, when a user attaches the housing case 11 of the external mechanism for endoscope 10 to the sub-operation portion 3S, the user confirms whether or not the second UD fixing handle 3h provided at the second UD knob 3g is in the free position, in advance.

Figure 6:
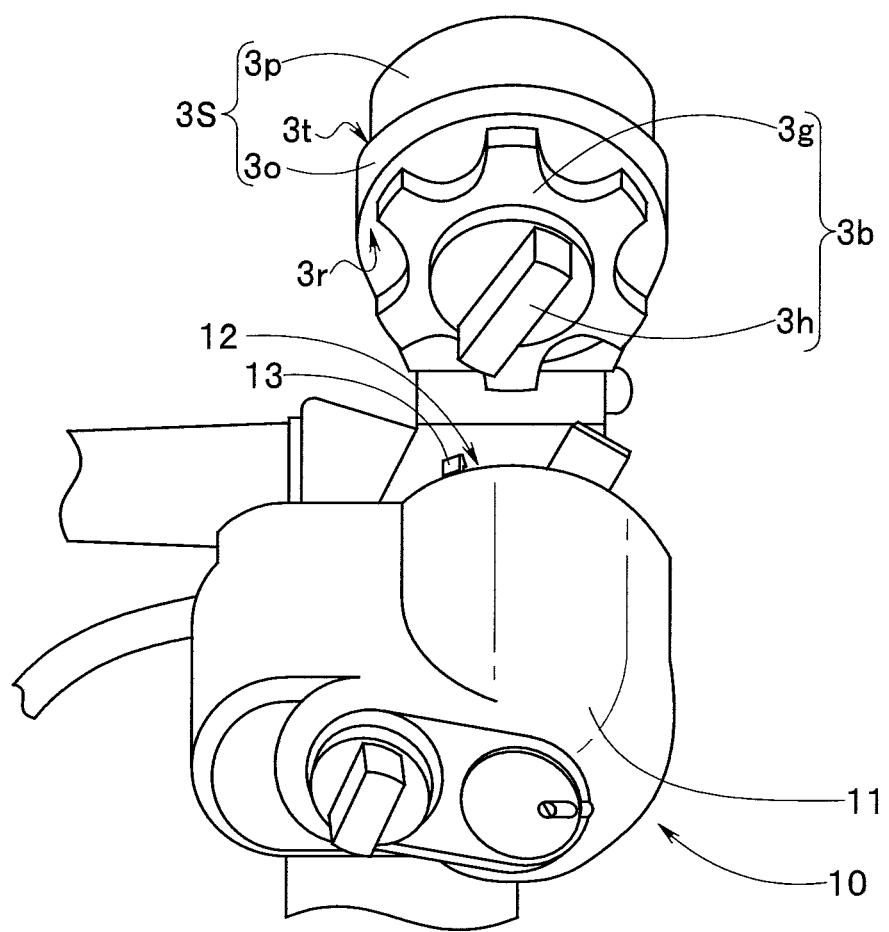
FIG. 6 is a diagram illustrating a manner in which the housing case of the external mechanism for endoscope is attached to the sub-operation portion.

After the user confirms that the second UD fixing handle 3h is arranged in the free position, as illustrated in FIG. 6, the user makes the case attaching/detaching section 12 of the housing case 11 face the knob arranging surface 3r of the sub-operation portion 3S. At this time, the user makes the bending wheel 41 of the knob rotating unit 40 disposed in the case inner space face the second UD knob 3g.

Next, the user moves the opening of the case attaching/detaching section 12 of the housing case 11 toward a ridge on the large-diameter portion end face 3r side of the sub-operation portion 3S. Then, an inclined surface 13c of each engaging portion 13b illustrated in FIGS. 4B and 4C mentioned above abuts on the ridge on the large-diameter portion end face 3r side of the large-diameter portion 3o and the elastically deforming portion 13a elastically deforms outwardly.

Subsequently, the user moves a ridge of a part in which the inclined surface 13c and the engagement surface 13d meet, on a surface of the large-diameter portion 3o in a direction toward the small-diameter portion 3p. Then, substantially simultaneously with the user bringing the abutment surface 14 into abutment with the large-diameter portion end face 3r, the ridge of the part in which the inclined surface 13c and the engagement surface 13d meet passes by the large-diameter portion 3o.

Then, a restoring force of the elastically deforming portion 13a makes the engaging portion 13b move in a direction toward a surface of the small-diameter portion 3p and the engagement surface 13d of the engaging portion 13b is locked on the large-diameter portion end face 3t via a snap-fit. As a result, the housing case 11 is fixedly provided on the sub-operation portion 3S and the attachment is thus completed.

In the attachment completed state, respective large parts of a circumferential surface on the large-diameter portion 3o side and a circumferential surface on the small-diameter portion 3p side of the sub-operation portion 3S and an end face of the small-diameter portion 3p of the sub-operation portion 3S are exposed to the outside.

In this way, the large-diameter portion end face 3t that forms the large-diameter portion 3o and the small-diameter portion 3b and has a function as a locking surface is provided in the sub-operation portion 3S. On the other hand, the plurality of locking members 13 are provided in the case attaching/detaching section 12 of the housing case 11. Each of the locking members 13 protrudes from the abutment surface 14 abutting on the knob arranging surface 3r of the sub-operation portion 3S, and includes an elastically deforming portion 13a and an engaging portion 13b including an engagement surface 13d.

Then, in a state in which the attachment of the housing case 11 to the sub-operation portion 3S has been completed, the engagement surface 13d of the engaging portion 13b arranged in each locking member 13 engages with the large-diameter portion end face 3t of the sub-operation portion 3S. Therefore, in the attachment completed state, in the sub-operation portion 3S, the sub-operation portion is not entirely covered by the housing case 11, but the respective large parts of the outer peripheral surface of the large-diameter portion 3o and the outer peripheral surface of the small-diameter portion 3p and the end surface of the small-diameter portion 3p of the sub-operation portion 3S are exposed to the outside. Therefore, the external mechanism for endoscope 10 including the housing case 11 can be reduced in weight.

As a result of the engaging portion 13b of each locking member 13, which protrudes from the abutment surface 14 of the housing case 11, being slid on the surface of the large-diameter portion 3o, the abutment surface 14 abuts on the large-diameter portion end face 3r and the engagement surface 13d engages with the large-diameter portion end face 3t, and thus, the attachment can easily be performed.

Then, disengagement between the abutment surface 14 and the large-diameter portion end face 3r enables the housing case 11 to be easily detached from the sub-operation portion 3S.

Figure 7:
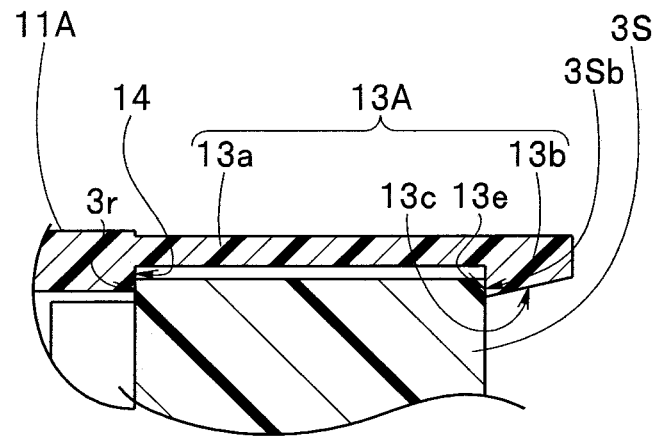
FIG. 7 is a diagram illustrating an example configuration in which instead of an end face of a large-diameter portion configured to function as a locking surface, a back surface of the sub-operation portion has a function of a locking surface.

Note that in the above-described embodiment, the large-diameter portion 3o and the small-diameter portion 3p are provided in the sub-operation portion 3S and the large-diameter portion end face 3t that functions as a locking surface configured to lock the engagement surface 13d of each engaging portion 13b is provided around the small-diameter portion 3p. However, as illustrated in FIG. 7, a back surface 3Sb of a sub-operation portion 3S, the back surface 3Sb being a surface that is adjacent to a knob arranging surface 3r across an outer peripheral surface, may have a function as a locking surface without providing the large-diameter portion 3o and the small-diameter portion 3p in the sub-operation portion 3S. The back surface 3Sb is a surface opposite to the knob arranging surface 3r and is also a second surface of the sub-operation portion 3S.

In other words, as with the above-described housing case 11, each locking member 13A included in the housing case 11A of another embodiment, which is illustrated in FIG. 7, includes an elastically deforming portion 13a and an engaging portion 13b in the order mentioned from the abutment surface 14 side.

In the present embodiment, the engaging portion 13b includes an inclined surface 13c that is similar to the above, and an engagement surface 13e that is locked on the back surface 3Sb instead of the large-diameter portion end face 3t. In other words, the locking member 13 and the locking member 13A are different from each other in terms of a distance from the abutment surface 14 to the engagement surface 13d and a distance from the abutment surface 14 to the engagement surface 13e.

The locking member 13A is similar to the above-described embodiment in terms of the rest of the configuration, and in the present embodiment, also, in a state in which attachment of the housing case 11A to the sub-operation portion 3S has been completed, the engagement surface 13e of each engaging portion 13b arranged at the locking member 13 engages with the back surface 3Sb of the sub-operation portion 3S. Therefore, in the attachment completed state, in the sub-operation portion 3S, the sub-operation portion is not entirely covered by the housing case 11A but a large part of an outer peripheral surface of the sub-operation portion 3S and a large part of the back surface 3Sb of the sub-operation portion 3S are exposed. Therefore, the external mechanism for endoscope 10 including the housing case 11A can be reduced in size.

Another example configuration of a housing case and a sub-operation portion will be described with reference to FIGS. 8A to 8C.

Figure 8A:
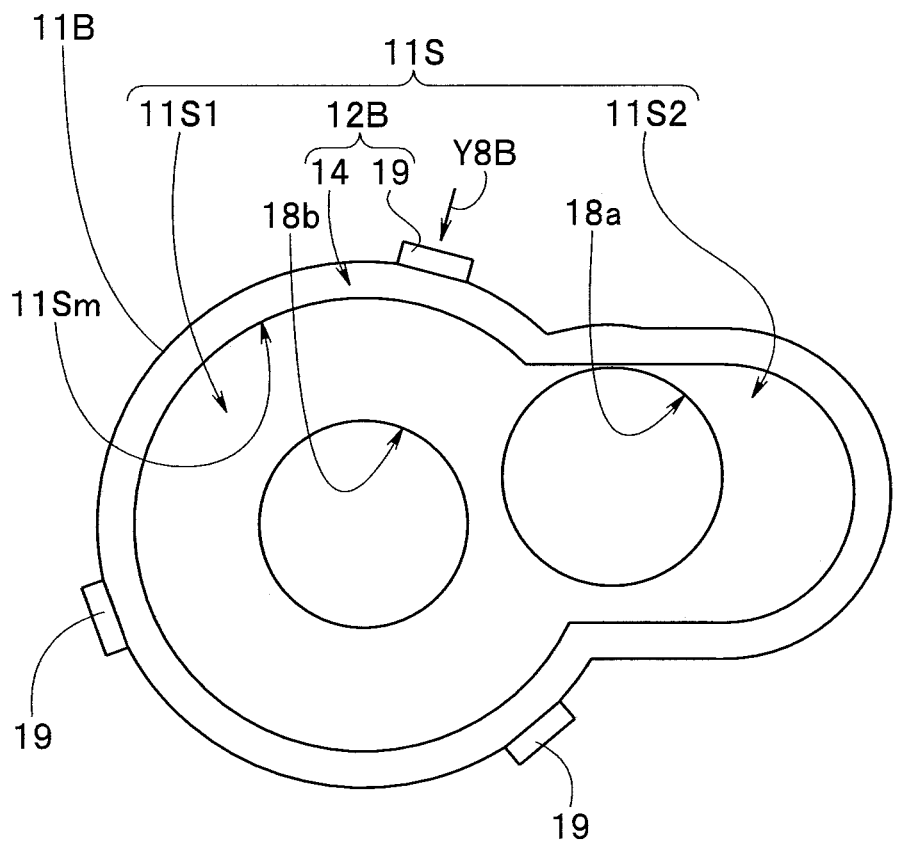
FIG. 8A is a diagram illustrating another example configuration of a housing case and a sub-operation portion and is a front view of the housing case.

As illustrated in FIG. 8A, a case attaching/detaching section 12B includes a plurality of locking projection portions 19. The plurality of locking projection portions 19 protrude from an outer peripheral surface of a housing case 11B including an engaging member disposing space 11S1, and are provided at respective predetermined positions at predetermined intervals or regular intervals in a circumferential direction. Note that the number of locking projection portions 19 is not limited to three but may be more than three, or two.

Figure 8B:
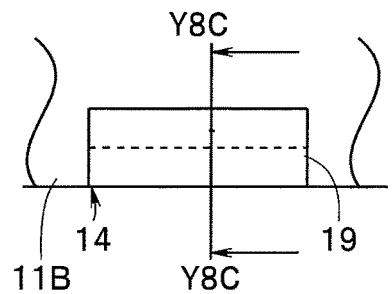
FIG. 8B is a view of a locking projection portion of the housing case as viewed in the arrow Y8B direction in FIG. 8A.
Figure 8C:
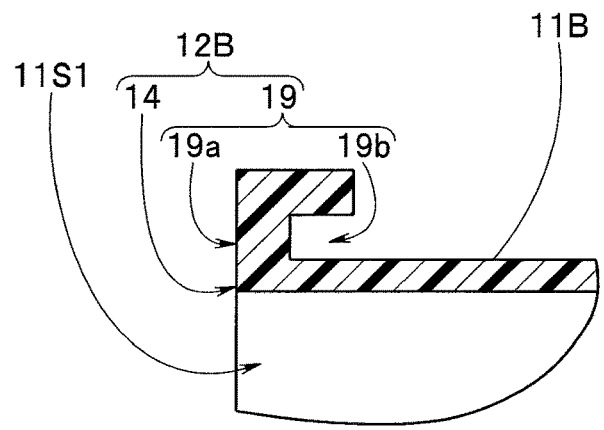
FIG. 8C is a sectional view along the arrow Y8C-Y8C line in FIG. 8B and is a diagram illustrating the locking projection portion.

As illustrated in FIGS. 8B and 8C, each locking projection portion 19 includes a projection portion end face 19a including an abutment surface 14 and an engaging groove 19b in which a locking member 60 is arranged. The rest of the configuration is similar to the above-described configuration and members that are the same as members in the above-described configuration are provided with reference numerals that are the same as the reference numerals in the above-described configuration and description of the members will be omitted.

Note that on the sub-operation portion 3S side to which the housing case 11B is attached, operation portion lugs (see reference numeral 3Sc in FIG. 8D) corresponding to the locking projection portions 19 are provided.

Figure 8D:
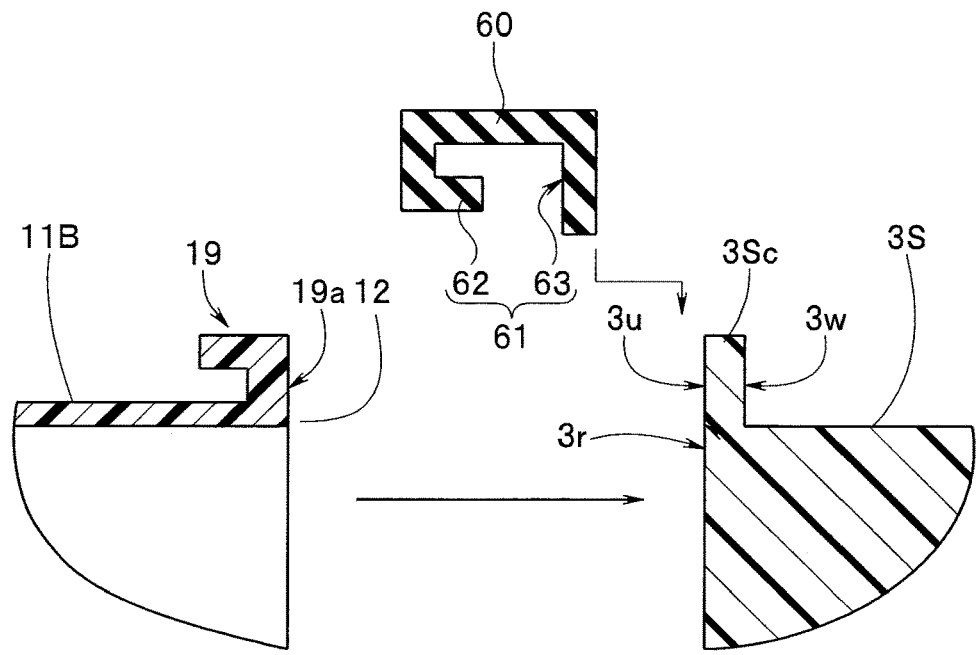
FIG. 8D is a diagram illustrating attachment of the sub-operation portion to the external mechanism for endoscope.

As illustrated in FIG. 8D, each operation portion lug 3Sc protrudes outwardly from a sub-operation portion outer peripheral surface by a predetermined amount. The amount of projection of each operation portion lug 3Sc from the sub-operation portion outer peripheral surface and an amount of projection of each locking projection portion 19 from the outer peripheral surface of the housing case 11B are similar to each other.

Note that reference numeral 60 denotes a locking member. Each locking member 60 is a member for fixing the housing case 11B and the sub-operation portion 3S integrally. Each locking member 60 includes an engaging groove 61 having a predetermined elastic force and a predetermined shape. Reference numeral 62 denotes an engaging projection portion and reference numeral 63 denotes a locking surface, and the engaging projection portion 62 and the locking surface 63 configure a part of the engaging groove 61.

Figure 8E:
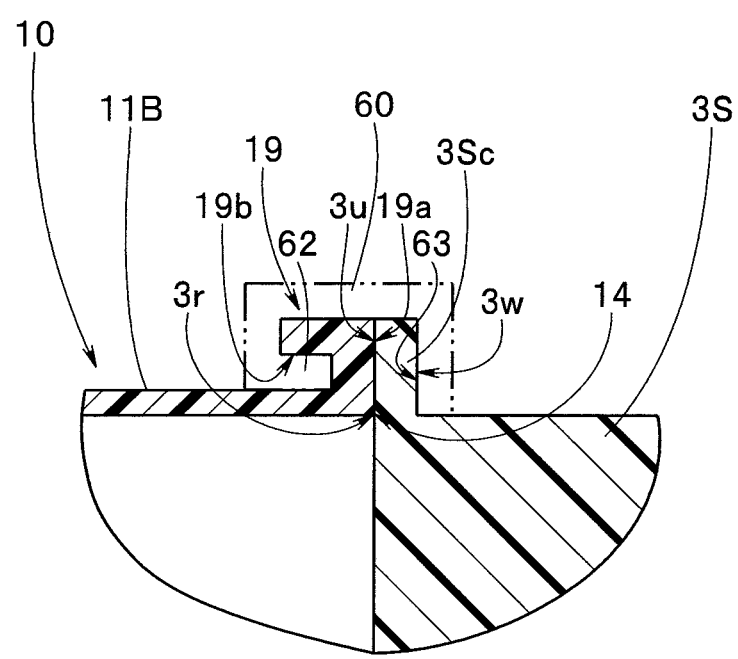
FIG. 8E is a diagram illustrating a state in which the housing case is fixedly provided on the sub-operation portion via locking members.

Attachment of an external mechanism for endoscope 10 to the sub-operation portion 3S will be described with reference to FIGS. 8D and 8E.

When a user attaches the external mechanism for endoscope 10 to the sub-operation portion 3S, as described above, the user confirms whether or not a second UD fixing handle 3h provided at a second UD knob 3g is in a free position, in advance.

After the confirmation, as illustrated in FIG. 8D, the user makes a case attaching/detaching section 12 of the housing case 11B face a knob arranging surface 3r of the sub-operation portion 3S.

Note that in FIG. 8D, e.g., the second UD knob 3g is omitted.

Next, the user moves the projection portion end faces 19a of the locking projection portions 19 provided at the housing case 11B toward a large-diameter distal end face 3u of the sub-operation portion 3S. Then, as illustrated in FIG. 8E, the user brings the projection portion end face 19a and the large-diameter distal end face 3u into abutment with each other.

In this abutment state, the user performs attachment of the locking members 60. In other words, the user arranges each of the engaging projection portions 62 forming the respective engaging grooves 61 included in the locking member 60 by sliding the engaging projection portion 62 along the corresponding engaging groove 19b and arranges each of the locking surfaces 63 forming the respective engaging grooves 61 by sliding along a proximal end side surface 3w that is an opposite surface of the relevant operation portion lug 3Sc from the knob arranging surface 3r. The proximal end side surface 3w is a second surface of the operation portion lug 3Sc.

As a result, as indicated by the alternate long and two short dashes line, each locking projection portion 19 of the housing case 11B and a corresponding operation portion lug 3Sc of the sub-operation portion 3S in which the projection portion end face 19a and the large-diameter distal end face 3u abut on each other are fixed integrally via an elastic force of the locking member 60, and thus, the housing case 11B is fixedly provided on the sub-operation portion 3S.

In this way, the operation portion lugs 3Sc are provided at the sub-operation portion 3S and the locking projection portions 19 are provided at the housing case 11B, and the locking members 60 for integrating the operation portion lugs 3Sc and the locking projection portions 19, respectively, are prepared. Then, in a state in which the projection portion end face 19a of each locking projection portion 19 of the housing case 11B is brought in abutment with the large-diameter distal end face 3u of the corresponding operation portion lug 3Sc of the sub-operation portion 3S, an engaging groove 61 of a locking member 60 is made to engage with the locking projection portion 19 and the operation portion lug 3Sc so as to cover the locking projection portion 19 and the operation portion lug 3Sc in a predetermined manner to complete the attachment.

In the attachment completed state, in the sub-operation portion 3S, the sub-operation portion is not entirely covered by the housing case 11B but a large part of an outer peripheral surface of the sub-operation portion and a large part of a proximal end surface of the sub-operation portion are exposed to the outside. Therefore, the external mechanism for endoscope 10 including the housing case 11B can be reduced in weight.

Appropriately setting an elastic force of the locking members 60 enables appropriately setting a strength of fixture between the sub-operation portion 3S and the housing case 11B to each other.

Note that in the attachment completed state, the housing case 11B can easily be detached from the sub-operation portion 3S by detaching the locking surface 63 of each locking member 60 from the corresponding proximal end side surface 3w.

Note that in the above-described embodiment, the plurality of locking members 13 are provided in the circumferential direction as locking claws. However, where a locking member 13 is made of an elastic member having an elastic force, an entire circumference of the outer peripheral surface of the sub-operation portion 3S may be covered by the locking member and the back surface 3Sb may be exposed alone.

In this case, appropriately setting the elastic force of the locking member that covers the entire circumference enables providing a locking portion in the locking member 13 or eliminating the need for a locking portion. Moreover, use of a highly-adhesive material such as a rubber case enables enhancement in fixing force using not only the elastic force but also a frictional force and thus enables reduction in covered area.

Note that in the above description, with the external mechanism for endoscope 10 fitted to the sub-operation portion 3S, an operation of bending the second bending portion 2b2 is performed without placing a large burden on the fingers of a user. However, the knob to which the external mechanism for endoscope 10 is fitted is not limited to the second UD knob 3g provided at the sub-operation portion 3S, but may be the first RL knob 3d provided at the main operation portion 3M or both the first UD knob 3c and the first RL knob 3d.

Note that the present invention is not limited only to the above-described embodiments but various modifications are possible without departing from the spirit of the invention.

What is claimed is:

1. An external mechanism for an endoscope, comprising:
   a first surface configured to cover a knob arranging surface at which a bending operation knob is arranged in an operation portion of the endoscope;
   an engaging member configured to engage with the bending operation knob of the endoscope, the bending operation knob being arranged on the knob arranging surface;
   a drive source configured to generate a driving force for rotating the engaging member;
   a housing case that houses the engaging member and the drive source;
   a case attaching/detaching and fixing section for detachably attaching the housing case to the operation portion of the endoscope; and
   a locking member provided at the housing case and configured to be locked on the knob arranging surface of the endoscope and a surface adjacent to the knob arranging surface in the operation portion of the endoscope.

2. The external mechanism for endoscope according to claim 1, wherein the locking member causes the housing case to be locked on the operation portion of the endoscope via a snap-fit.

3. The external mechanism for endoscope according to claim 1, wherein the locking member causes the housing case to be locked on the operation portion of the endoscope by the locking member being slid along an operation portion lug provided at the operation portion of the endoscope.

4. The external mechanism for endoscope according to claim 1, wherein the locking member is arranged on the first surface or a second surface adjacent to the first surface.

5. The external mechanism for endoscope according to claim 1, wherein the locking member causes an outer peripheral surface and an opposite surface that are adjacent to the knob arranging surface in the operation portion of the endoscope to be exposed to an outside.

6. An endoscope apparatus comprising:
   an endoscope that includes an operation portion including a bending operation knob configured to perform an operation of bending a bending portion, and a knob arranging surface at which the bending operation knob is arranged; and
   an external mechanism for the endoscope, the external mechanism including a first surface configured to cover the knob arranging surface of the endoscope, an engaging member configured to engage with the bending operation knob of the endoscope, the bending operation knob being arranged at the knob arranging surface, a drive source configured to generate a driving force for rotating the engaging member, a housing case that houses the engaging member and the drive source, a case attaching/detaching and fixing section for detachably attaching the housing case to the operation portion of the endoscope, and a locking member provided at the housing case and configured to be locked on the knob arranging surface of the endoscope and a surface adjacent to the knob arranging surface in the operation portion of the endoscope.

* * * * *